United States Patent
Hansen

(10) Patent No.: US 8,048,677 B2
(45) Date of Patent: Nov. 1, 2011

(54) SENSOR BOARD

(75) Inventor: Michael Svendsmark Hansen, Frederiksberg (DK)

(73) Assignee: Radiometer Medical ApS, Bronshoj (DK)

( * ) Notice: Subject to any disclaimer, the term of this patent is extended or adjusted under 35 U.S.C. 154(b) by 275 days.

(21) Appl. No.: 12/081,998

(22) Filed: Apr. 24, 2008

(65) Prior Publication Data
US 2008/0266545 A1 Oct. 30, 2008

(30) Foreign Application Priority Data

Apr. 27, 2007 (EP) .................................. 07388029

(51) Int. Cl.
*G01N 33/50* (2006.01)
(52) U.S. Cl. .......... 436/68; 436/127; 436/136; 436/138; 422/400; 422/82.01; 422/82.05; 356/39; 250/458.1
(58) Field of Classification Search .................... None
See application file for complete search history.

(56) References Cited

U.S. PATENT DOCUMENTS

| | | | |
|---|---|---|---|
| 4,557,900 A | 12/1985 | Heitzmann | |
| 4,786,474 A | 11/1988 | Cooper | |
| 5,141,868 A * | 8/1992 | Shanks et al. | 435/287.9 |
| 5,208,147 A * | 5/1993 | Kagenow et al. | 435/14 |
| 5,525,518 A | 6/1996 | Lundsgaard et al. | |
| 5,564,419 A * | 10/1996 | Lundsgaard et al. | 600/317 |
| 5,601,743 A * | 2/1997 | Mednikov et al. | 219/635 |
| 5,627,922 A * | 5/1997 | Kopelman et al. | 385/12 |
| 6,123,820 A | 9/2000 | Bergkuist | |
| 2004/0156192 A1* | 8/2004 | Kerr et al. | 362/154 |
| 2005/0106074 A1 | 5/2005 | Sakamoto | |

FOREIGN PATENT DOCUMENTS

| | | |
|---|---|---|
| EP | 0 545 284 A1 | 6/1993 |
| EP | 1 054 257 A | 6/1993 |
| WO | WO 94/18559 A | 8/1994 |

* cited by examiner

*Primary Examiner* — Yelena G Gakh
*Assistant Examiner* — Michelle Adams
(74) *Attorney, Agent, or Firm* — Morgan, Lewis & Bockius LLP

(57) ABSTRACT

The invention relates to a sensor board comprising a plate-like body comprising a body material and having two surfaces substantially parallel to each other, and at least one optical sensor and at least one non-optical sensor, the sensors being positioned at the same surface of the body, wherein the body includes a first area having a thickness $D_1$ of the body material and a second area having a thickness $D_2$ of the body material, where $D_1 > D_2 > 0$, the at least one optical sensor being positioned at the second area.

20 Claims, 2 Drawing Sheets

SENSOR BOARD

BACKGROUND OF THE INVENTION

The invention relates to a sensor board comprising a plate-like body comprising a body material and having two surfaces substantially parallel to each other, and at least one optical sensor and at least one non-optical sensor, where the sensors are positioned at the same surface of the body, In this context the term sensor board denotes a board of solid material carrying two or more sensors on at least one surface of the board.

Optical sensors are widely used in analytical devices for analyzing samples within several technical fields, e.g. for assessing the quality of food and drinking products or industrial products.

Optical in vitro determination of parameters in a blood sample is normally performed by means of blood gas analyzers as, e.g. the blood gas analyzers produced and sold by Radiometer Medical ApS, Copenhagen, Denmark, under the name ABL800 FLEX. In these analyzers the optical sensors are normally installed as self-contained photometric units and require space and, furthermore, make the analyzing path longer, which again may require larger samples.

Due to the tendency of minimizing the amount of blood required for measurements, which is particularly true for critically ill patients for which many subsequent samples may be required and neonates for which the available amount of blood is highly limited, it is desired to minimize the analyzing path e.g. by providing as many sensors for analyzing different parameters in as little volume as possible.

Also in other applications the requirement for minimal sample volume may be relevant, e.g. when specimen from where the sample is derived is sparse or expensive. Consequently, it would be a significant advantage if optical sensors could be combined with other sensors on a sensor board.

BRIEF SUMMARY OF THE INVENTION

The object of the present invention is to provide a sensor board including at least an optical sensor, which sensor board may carry all the sensors necessary for a desired analysis and at the same time is very compact.

The present invention also provides a sensor board, which makes it possible to minimize the analyzing path and obtain reliable results on a minor amount of sample. Moreover, the sensor board according to the invention does not require a sealing around the area where the optical sensor is located, which simplify the manufacturing process, and significantly reduces the risk of leakage.

The optical sensor board according to the invention comprises at least one integrated optical sensor and by integrating optical sensors the space required for sensors may be reduced.

Thus, in the sensor board according to the invention the body includes a first area having a thickness $D_1$ of the body material and a second area having a thickness $D_2$ of the body material, where $D_1 > D_2 > 0$, the at least one optical sensor being positioned at the second area.

The thickness $D_2$ of the second area is a thickness that is reduced compared with the thickness $D_1$ of the first area. However, the thickness $D_2$ of the second area is a thickness that provides for a sufficient strength of the second area, e.g. in respect of carrying sensors or other material. Preferably the second area only constitutes a minor part of the sensor board and preferably the second area is placed away from the edges of the sensor board. This will ensure that the sensor board as such maintains a sufficient strength in use.

That the sensor board is plate-like means that the sensor board has the shape as a thin plate or sheet and preferably a substantially rectangular shape.

The invention is based on the unexpected finding that it is possible to make an opaque sensor board translucent in at least a limited area by reducing the thickness of the sensor board in that area to a thickness $D_2$ which is smaller than the general all over thickness $D_1$. Hitherto it has been presumed that reducing the thickness to a degree that makes a sensor board translucent would adversely affect the strength of the sensor board.

Contrary to the above-mentioned presumption it has now appeared that is it possible to reduce the thickness of a sensor board in at least a limited area to a thickness $D_2$, where $D_1 > D_2 > 0$, while substantially maintaining the strength of the sensor board.

The thickness of the sensor board is reduced to a thickness $D_2$ in the second area and to a degree that makes the sensor board sufficiently translucent for electromagnetic radiation at a desired wavelength in that area.

The bottom part in the second area, i.e. the remaining material, may be considered as forming a translucent area for an optical sensor system. To form a translucent area in this way provides the advantage that packing around the translucent area is superfluous as there is no passageway that needs to be packed. Thereby the risk of leakage and contamination is significant reduced.

Preferably, the optical sensor communicates with an optical sensor system positioned at the second area.

Preferably the optical sensor system comprises an emitter for emitting a beam of electromagnetic radiation. The emitted electromagnetic radiation may be detected directly or indirectly by a detector in the optical sensor system. Moreover, the detector may detect reflected electromagnetic radiation or a change in the electromagnetic radiation. The electromagnetic radiation may in principle be any electromagnetic radiation with any wave length, such as ultraviolet light, infrared light, visible light, x-rays etc.

Of course the sensor board may comprise more than one second area with thickness $D_2$ for optical sensors if desired. In principal the number may be unlimited, in practical the number will be limited to from one to about twelve or two, three, four, five, six, seven or eight areas with the thickness $D_2$. The areas with thickness $D_2$ may be produced by conventional means, such as cutting, grinding, drilling or by laser or sonic treatment, optionally with a final polishing of the bottom part. The sensor board may also be produced by adhering different layers together in a laminated structure, e.g. a first thin translucent layer laminated to a thicker second layer with a through going hole. The second area with thickness $D_2$ will then be formed by the first thin layer at the position of the through going hole in the second layer.

The second area with thickness $D_2$ suitably has a circular cross-section, however, other cross-sections like oval, square, rectangular etc. may also be suitable.

It may also be envisaged that in alternative embodiments the sensor board may comprise areas with thickness $D_3$, where $D_1 < D_3 < 0$, and $D_3$ is different from $D_2$. Several such areas with different thicknesses $D_4$, $D_5$, $D_6$ etc. may be considered. Such embodiments may e.g. be useful when using different optical sensors that each requires a different thickness $D_3$, $D_4$ etc. of the board.

Preferably, the sensor board comprises a plurality of non-optical sensors arranged on the first surface of the sensor board. The plurality of non-optical sensors may comprise one, two, three, four, five, six, seven or a further plurality of non-optical sensors on the same surface. The term non-optical sensor as used herein is any kind of sensor that may be used to detect and measure the amount of a desired parameter using non-optical measures. A non-optical sensor normally comprises one or more electrodes in a capsule closed by one or more membranes. The non-optical sensors arranged on the same surface are preferably applied by thick film technique. Preferably the non-optical sensors are selected among potentiometric sensors and amperometric sensors.

By this configuration wherein non-optical and optical sensors are combined a very compact unit is achieved compared with traditional analyzers, where each sensor constitute a unit by it self. Thus, less space is required for the sensors and smaller sample sizes are required.

To serve as a suitable substrate for thick film appliance it is preferred that the body material is heat-resistant, preferably heat resistant to a temperature above 200° C., more preferably above 400° C., even more preferably above 600° C. Suitably the body material is heat-resistant to a temperature above 800° C. or even above 1000° C.

Although the sensor board may be made from several materials, such as ceramic, glass, polymer, metal or combinations thereof it is preferred that the sensor board is made from a ceramic material. The ceramic material may be selected from alumina, aluminum oxide, silicon carbide, boron nitride, silicon nitride and similar materials or mixtures thereof. Such materials are known to have excellent strength and properties e.g. in respect of carrying electrical wiring etc. At present the preferred ceramic material is alumina, which provides an excellent substrate for thick-film application.

The thickness $D_1$ is normally in the range of 0.3 mm to 2.5 mm, preferably in the range of 0.5 mm to 1 mm.

To obtain satisfactory properties of the optical sensor on the sensor board according to the invention the thickness $D_2$ is preferably less than about 0.5 mm. Further, to obtain even better properties it is preferred that the thickness $D_2$ is within the range of about 0.05 mm to about 0.5 mm.

Preferably the thickness $D_2$ is sufficiently thin to inhibit a possible luminescence arising from the material of the sensor board from interfering with an optical measurement. This will reduce the sources of errors in the optical system.

In a preferred embodiment according to the invention the sensor board is coated with a layer of a luminophor at least partly overlapping the second area with thickness $D_2$. Preferably, the luminophor has been dispensed directly onto the sensor board at the area with thickness $D_2$.

In a preferred embodiment, the thickness $D_2$ of the sensor board is sufficiently small to prevent or at least significantly reduce or inhibit a possible luminescence arising from the material of the sensor board from interfering with a measurement of luminescence arising from the luminophor. In this manner a further source of error in the measurement may be eliminated.

Preferably, the optical sensor system comprises a detector for detecting luminescence generated by the luminophor. The emitter for applying electric radiation may e.g. be a light emitting diode or bulb. The source preferably applies electric radiation with a wavelength in the range of about 519 nm. The means for detecting luminescence generated by the luminophor may e.g. suitable be an optical detector capable of detecting radiation within the wavelength e.g. about 672 nm generated by the luminophor. The luminophor material is preferably applied on the surface of the sensor board being in contact with the sample so that constituents in the sample may quench the excited luminophor material, which will shorten the lifetime of the excited state.

Furthermore, in a preferred embodiment of the sensor board, the thickness $D_2$ is sufficiently thin to allow a significant part of a beam of electromagnetic radiation having a wavelength being adapted to excite the luminophor to pass the sensor board at the position of the thickness $D_2$.

In a further preferred embodiment of the sensor board the optical sensor is intended for measuring oxygen and the luminophor preferably is of a kind having its luminescence quenched by oxygen. When the sensor board e.g. is intended for measuring on physiological fluids like blood it is desirable among other parameters to determine the content of oxygen in the blood.

It has been known for some years to determine the content of molecular oxygen in a sample by using optical methods based on luminescence quenching. In general, these methods comprise measuring the luminescence intensity and/or the luminescence lifetime of a suitable luminophor, the luminophor being in contact with an oxygen-containing sample and being exposed to illumination. The basic feature of luminescence quenching is the deactivation of the luminescing excited electronic state of the luminophor taking place on collision with oxygen molecules. As the average number of luminophor molecules in the excited electronic state is reduced by the interaction with the oxygen molecules, the luminescence intensity and the excited state lifetime of the luminophor are reduced. The magnitude of the reduction is connected with the number of oxygen molecules in contact with the luminophor through the Stern-Volmer equation $$M^0/M = 1 + K_{Sv}[O_2]$$

$M^0$ and $M$ of the above equation designate the luminescence intensity or the excited state lifetime of the luminophor in the absence and presence of oxygen, respectively. $[O_2]$ designates the concentrations of molecular oxygen corresponding to the M-value measured. $K_{Sv}$ is the so-called Stern-Volmer constant. By using this equation and correlating it to samples of known oxygen content, it is possible to determine the oxygen content of a sample. Photometric determination of the oxygen content in blood or other media by the so-called luminescence quenching is known from e.g. U.S. Pat. No. 5,242,835 to Jensen et al. which discloses a photometric analysis of oxygen by an in vitro method for determination of oxygen in discrete samples and based on simple sample handling principles. U.S. Pat. No. 5,242,835 is hereby incorporated by reference.

The optical sensor is adapted to be positioned with the luminophor layer in fluid contact with a fluid sample in order to detect a partial pressure of a constituent present in the fluid sample. Thus, it is preferred that the luminophor layer is a part of the analyzing pathway in contact with the sample to be analyzed.

In determination of the oxygen concentration it is desired that a preferred material for the luminophor layer comprises a palladium-porphyrin, e.g. palladium(II)-tetraphenylporphyrin (PdTPP) or palladium(II)-(pentafluorohenyl)-porphyrin (PdTFPP).

Consequently, in a preferred embodiment the optical sensor is adapted for measuring the content of oxygen in a sample.

Preferably, an emitter for emitting a beam of electromagnetic radiation having a wavelength being adapted to excite the luminophor is adapted on the surface of the sensor board not carrying sensors in the second area with thickness $D_2$. In this embodiment, the emitter and the detector are adapted at the same surface of the sensor board, thus facilitating the connection of the board with the optical sensors.

Alternatively, two opposing sensor boards may be arranged with the first surfaces facing each other and the second areas with thickness $D_2$ facing each other in such a way that an electromagnetic beam may pass through the areas with thickness $D_2$ on both sensor boards.

In such a configuration the sensor boards are capable of functioning as an optical measuring cell that also includes one or more electrochemical sensors. In the embodiment one or both of the sensor boards may carry one or more electrochemical sensors. In this manner one or more optical sensors and one or more electrochemical sensors may be present in a diminutive volume and, consequently, smaller samples may be measured by the optical sensor system.

The invention also relates to use of a sensor board, wherein the at least one optical sensor interacts with an optical detector system.

The sensor board is useful for measuring a partial oxygen pressure in a fluid sample. In particular use of the optical sensor board for measuring partial oxygen pressure in a blood sample is advantageously. Consequently, the optical sensor board is suitable for use in photometric in vitro determination of the content of oxygen in a blood sample.

BRIEF DESCRIPTION OF THE SEVERAL VIEWS OF THE DRAWINGS

The invention will now be explained in further details with reference to drawings in which.

DETAILED DESCRIPTION OF THE INVENTION

Figure 1:
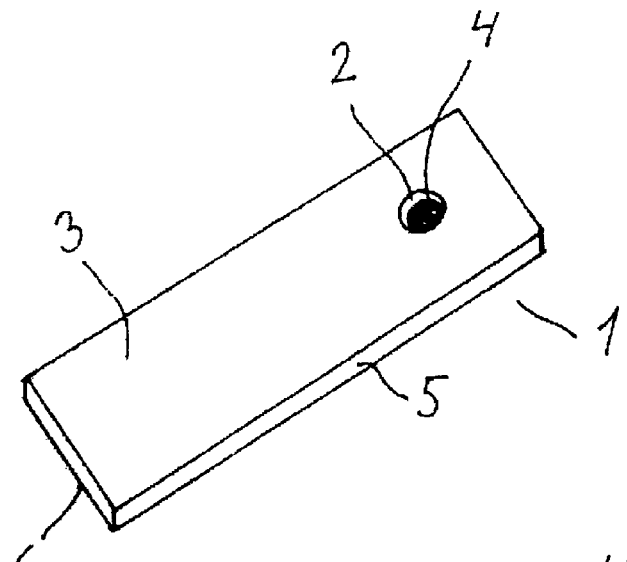
FIG. 1 shows a sensor board according to the invention.

In FIG. 1 is seen a depiction of a sensor board 1 for use according to the invention. The sensor board 1 has a surface 6 (facing downwards and not visible in the figure) and a surface 3. The two surfaces 6 and 3 are substantially parallel and the distance between them defines an overall thickness $D_1$ denoted 5 of the sensor board 1. In the surface 3 the sensor board 1 has a recess 2 which is limited downwards by the bottom part 4. The thickness of the bottom part 4, which is the result of a reduction of the overall thickness $D_1$ of the sensor board at the location of the recess 2, is reduced to a thickness $D_2$ that makes the bottom part 4 sufficiently transparent to an electromagnetic beam.

Figure 2:
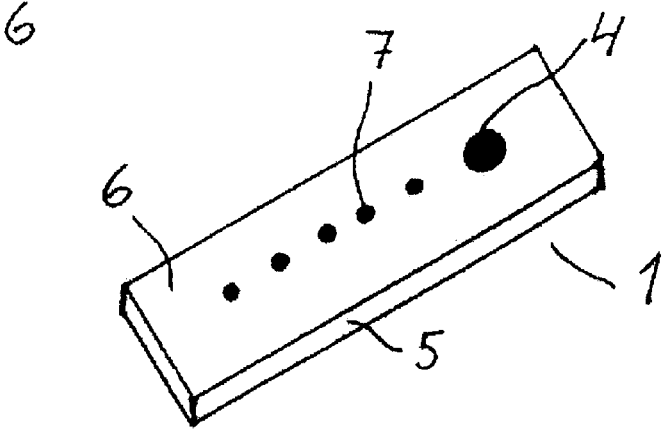
FIG. 2 shows a sensor board according to the invention.

FIG. 2 shows the sensor board 1 seen towards the surface 6. The area of the sensor board 1 with thickness $D_2$ is coated with a layer of luminophor 8. Five electrochemical sensor elements 7 are indicated on the first surface 6 of the sensor board 1.

The sensor board depicted in FIG. 1 and FIG. 2. is made from ceramic aluminum oxide which provides good strength. The sensor board has the dimensions: length approx 4.3 mm, width approx. 8 mm, thickness $D_1$ approx 0.8 mm. The thickness $D_2$ is approx. 0.1 mm. The diameter of the recess 2 constituting the part of the sensor board 1 with reduced thickness $D_2$ is approx. 2.8 mm. The recess 2 has been formed by drilling in the sensor board 1 from the second surface 3 towards the first surface 6 with a diamond drill. The sensor elements 7 are applied by thick film technique.

Figure 3:
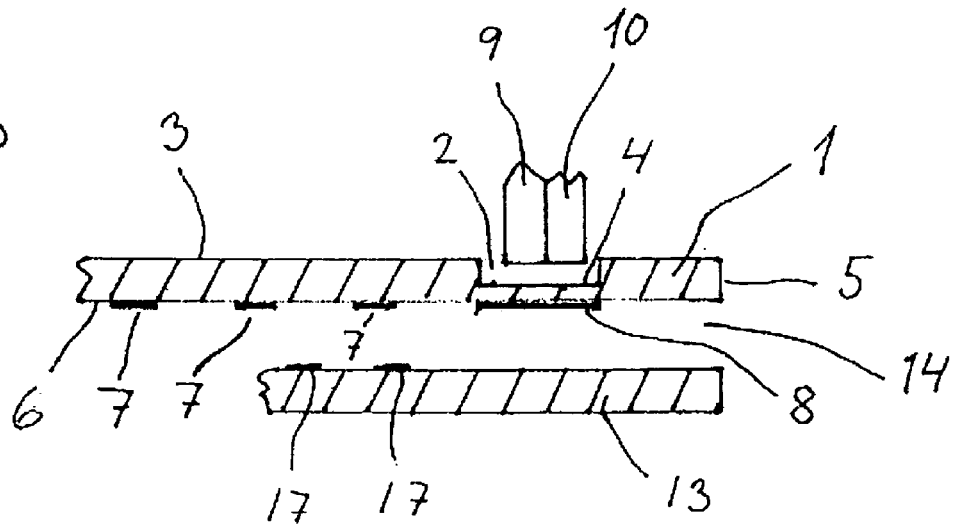
FIG. 3 shows a cut through an optical sensor system applied with a sensor board according to the invention.

FIG. 3 displays a cut through an optical sensor system with the sensor board 1 with recess 2 in the surface 3 and bottom part 4 in the recess 2. In the area of the bottom part 4 on the surface 6 is applied a layer of luminophor 8. Above the bottom part 4 is indicated a source for electromagnetic radiation 9 beside a detector 10 for detecting luminescence from the luminophor 8. The thickness $D_1$ denoted 5 of the board is clearly shown. Moreover, the surface 6 of the sensor board 1 comprises sensor elements 7 for the determination of desired parameters. The sensor elements 7 are applied by thick film technique. FIG. 3 also indicates an opposing board 13, which is part of a channel 14 constituting an analyzing path. The board 13 also comprises sensor elements 17. The layer of luminophor 8 and the sensor elements 7 and 17 of the two boards 1 and 13 are in direct contact with a sample flowing in the channel 14.

Figure 4:
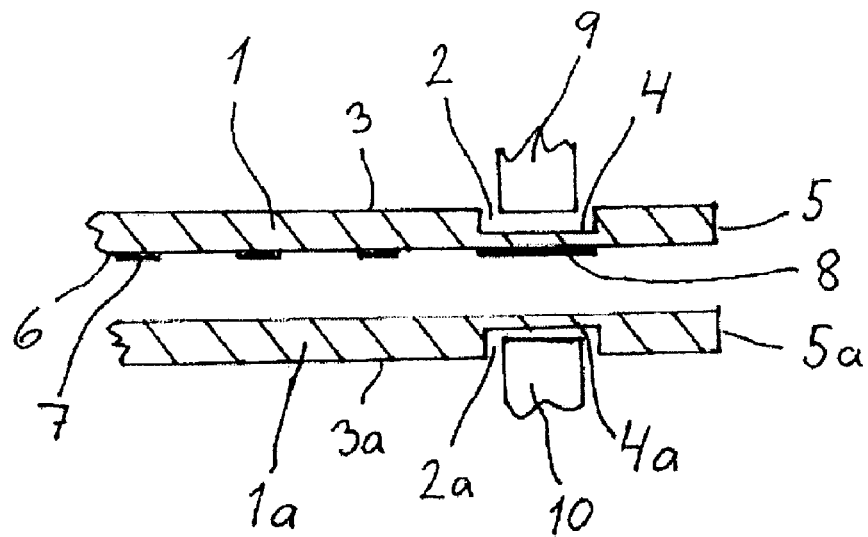
FIG. 4 shows an alternative embodiment of the optical sensor system.

FIG. 4 shows an alternative embodiment of the optical sensor system. The system comprises two opposing boards 1 and 1a according to the invention, both having a recess 2 and 2a with a bottom part 4 and 4a having reduced thickness $D_2$ when compared with the overall thickness $D_1$ denoted 5 and 5a of the sensor boards 1 and 1a, respectively. Furthermore, the sensor board 1 on the second surface 6 is coated with a luminophor 8 covering the area 4 with thickness $D_2$ and comprises sensor elements 7.

On the second surface 3 of the sensor board 1 is adapted an emitter 9 for electromagnetic radiation. On the second surface 3a of sensor board 1a is adapted a detector 10.

Figure 5:
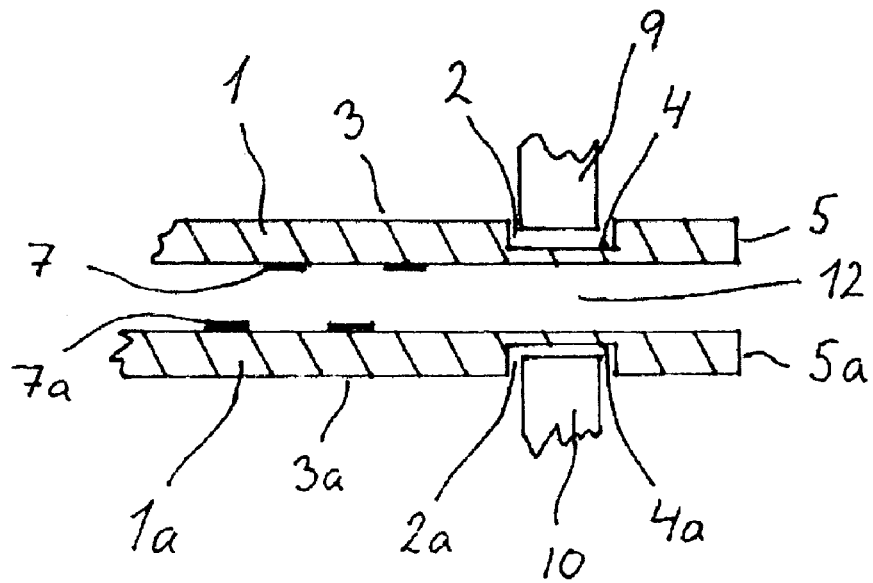
FIG. 5 shows a further alternative embodiment of the optical sensor system.

FIG. 5 shows a further embodiment of the optical sensor system similar to the embodiment of FIG. 4 and with reference numbers referring to the same parts of the optical sensor system. The optical sensor system of FIG. 4 distinguish from the optical sensor system of FIG. 5 in that the areas with thickness $D_2$ are not coated with a luminophor and the space 12 between the two sensor boards 1 and 1a functions as an optical measuring cell. Thus electromagnetic radiation emitted from emitter 9 positioned at the second surface 3 of the board 1 is passed through the sample in the space 12 and the resulting radiation detected by the detector 10 positioned at the second surface 3a of the board 1a. Moreover, in this embodiment the sensor board 1a comprises sensor elements 7a.

Of course the sensor board is part of an analyzing device that comprises many other parts, such as analyzing devices, pumps, and thermo elements etc., which are all well-known to the skilled person, who will also be familiar with how the sensor board combines with the other parts. Furthermore, the skilled person would be able to point out further embodiments of the sensor board according to the invention and an optical sensor system communicating therewith.

The invention claimed is:

1. A sensor board comprising:
   a plate-like body comprising a body material and having two surfaces substantially parallel to each other, and
   at least one optical sensor and at least one non-optical sensor, the sensors being positioned on the same surface of the body,
   wherein the body includes a first area having a thickness $D_1$ of the body material that is opaque to electromagnetic radiation of a desired wavelength and a second area having a thickness $D_2$ of the body material that is translucent to electromagnetic radiation of the desired wavelength, where $D_1 > D_2 > 0$, the at least one optical sensor being positioned at the second area to receive electromagnetic radiation of the desired wavelength transmitted through the second area of the body and the at least one non-optical sensor being an electrochemical sensor positioned at the first area.

2. The sensor board according to claim 1, wherein the at least one non-optical sensor is selected among potentiometric sensors and amperometric sensors.

3. The sensor board according to claim 1, wherein a plurality of non-optical sensors are arranged on the body.

4. The sensor board according to claim 1, wherein the body material is heat-resistant.

5. The sensor board according to claim 1, wherein the body material is heat-resistant to a temperature above 200° C.

6. The sensor board according to claim 1, wherein the body material is heat-resistant to a temperature above 400° C.

7. The sensor board according to claim 1, wherein the plate-like body is made from a ceramic material.

8. The sensor board according to claim 7, wherein the thickness $D_1$ is in the range of 0.8 to 2.5 mm.

9. The sensor board according to claim 8, wherein the thickness $D_2$ is less than 0.4 mm.

10. The sensor board according to claim 7, wherein the thickness $D_2$ is less than 0.4 mm.

11. The sensor board according to claim 7, wherein the thickness $D_2$ is within the range of 0.05 mm to 0.3 mm.

12. The sensor board according to claim 1, wherein the at least one optical sensor is an oxygen sensor.

13. The sensor board according to claim 1, wherein the at least one optical sensor comprises a layer of a luminophor.

14. The sensor board according to claim 13, wherein the luminophor has its luminescence quenched by oxygen.

15. The sensor board according to claim 14, wherein the luminophor layer comprises a palladium-porphyrin.

16. A method of using the sensor board according to claim 1, comprising:
    measuring an oxygen content of a sample using the sensor board of claim 1, wherein the at least one optical sensor interacts with an optical detector system.

17. A method of using the sensor board according to claim 1, comprising:
    measuring an oxygen content of blood using the sensor board of claim 1, wherein the at least one optical sensor interacts with an optical detector system.

18. A method of using the sensor board according to claim 13, comprising:
    measuring an oxygen content of a sample using the sensor board of claim 13, wherein the at least one optical sensor interacts with an optical detector system.

19. A method of using the sensor board according to claim 13, comprising:
    measuring an oxygen content of blood using the sensor board of claim 13, wherein the at least one optical sensor interacts with an optical detector system.

20. A method of using the sensor board according to claim 15, comprising:
    measuring an oxygen content of blood using the sensor board of claim 15, wherein the at least one optical sensor interacts with an optical detector system.

* * * * *